(12) United States Patent
Lin

(10) Patent No.: US 7,275,545 B2
(45) Date of Patent: Oct. 2, 2007

(54) METHODS AND APPARATUS FOR PRESBYOPIA CORRECTION USING ULTRAVIOLET AND INFRARED LASERS

(75) Inventor: Jui Teng Lin, Oviedo, FL (US)

(73) Assignee: Surgilight, Inc., Oviedo, FL (US)

( * ) Notice: Subject to any disclaimer, the term of this patent is extended or adjusted under 35 U.S.C. 154(b) by 273 days.

(21) Appl. No.: 11/002,929

(22) Filed: Dec. 2, 2004

(65) Prior Publication Data

US 2005/0107774 A1 May 19, 2005

Related U.S. Application Data

(63) Continuation of application No. 09/820,832, filed on Mar. 30, 2001, now abandoned, which is a continuation-in-part of application No. 09/303,673, filed on May 3, 1999, now Pat. No. 6,258,082.

(51) Int. Cl.
*A61B 19/00* (2006.01)
*A61B 18/20* (2006.01)

(52) U.S. Cl. .......................... 128/897; 606/5

(58) Field of Classification Search ............... 606/4–6; 128/898
See application file for complete search history.

(56) References Cited

U.S. PATENT DOCUMENTS

| | | | |
|---|---|---|---|
| 4,592,065 A | 5/1986 | de Witte | |
| 4,755,999 A | 7/1988 | Macken | |
| 4,773,414 A | 9/1988 | L'Esperance, Jr. | |
| 4,846,172 A | 7/1989 | Berlin | |
| 4,907,586 A | 3/1990 | Bille et al. | |
| 5,019,074 A | 5/1991 | Muller | |
| 5,102,409 A | 4/1992 | Balgorod | |
| 5,108,388 A | 4/1992 | Trokel | |
| 5,144,630 A | 9/1992 | Lin | |
| 5,152,760 A | 10/1992 | Latina | |
| 5,163,934 A | 11/1992 | Munnerlyn | |
| 5,354,331 A | 10/1994 | Schachar | |
| 5,423,801 A | 6/1995 | Marshall et al. | |
| 5,465,737 A | 11/1995 | Schachar | |
| 5,484,432 A | 1/1996 | Sand | |
| 5,489,299 A * | 2/1996 | Schachar | 623/4.1 |
| 5,490,849 A | 2/1996 | Smith | |
| 5,503,165 A * | 4/1996 | Schachar | 128/898 |
| 5,520,679 A | 5/1996 | Lin | |
| 5,529,076 A | 6/1996 | Schachar | |
| 5,533,997 A | 7/1996 | Ruiz | |
| 5,549,598 A | 8/1996 | O'Donnell, Jr. | |

(Continued)

FOREIGN PATENT DOCUMENTS

WO    WO 98/41177    9/1998

*Primary Examiner*—A. Farah
(74) *Attorney, Agent, or Firm*—Knobbe, Martens, Olson & Bear LLP

(57) ABSTRACT

Presbyopia is treated by a system using various lasers to remove a portion of the scleral tissue and increase the accommodation of the presbyopic patient's eye. Stable accommodation is achieved by the filling of the sub-conjunctiva tissue to the laser-ablated scleral areas. The proposed laser wavelength ranges from ultraviolet to infrared of (0.15-0.36) microns, (0.5-1.4) microns and (0.9-3.2) microns. Both scanning and fiber delivered systems are proposed to generate the ablation patterns. Laser ablation of the sclera may be conducted with or without opening the conjunctiva layer.

39 Claims, 2 Drawing Sheets

U.S. PATENT DOCUMENTS

| | | |
|---|---|---|
| 5,599,341 A | 2/1997 | Mathis et al. |
| 5,630,810 A | 5/1997 | Machat |
| 5,722,952 A | 3/1998 | Schachar |
| 5,738,676 A | 4/1998 | Hammer et al. |
| 5,741,247 A | 4/1998 | Rizoiu et al. |
| 5,782,822 A | 7/1998 | Telfair et al. |
| 5,803,923 A | 9/1998 | Singh-Derewa et al. |
| 5,845,024 A | 12/1998 | Tsushima et al. |
| 5,891,131 A | 4/1999 | Rajan et al. |
| 5,928,129 A | 7/1999 | Ruiz |
| 5,984,916 A | 11/1999 | Lai |
| 5,997,529 A | 12/1999 | Tang et al. |
| 6,010,497 A | 1/2000 | Tang et al. |
| 6,019,754 A | 2/2000 | Kawesch |
| 6,090,100 A | 7/2000 | Hohla |
| 6,090,102 A | 7/2000 | Telfair et al. |
| 6,099,522 A | 8/2000 | Knopp et al. |
| 6,132,424 A | 10/2000 | Tang |
| 6,146,375 A * | 11/2000 | Juhasz et al. .................. 606/6 |
| 6,156,030 A | 12/2000 | Neev |
| 6,161,546 A | 12/2000 | Yavitz |
| 6,171,336 B1 | 1/2001 | Sawusch |
| 6,190,374 B1 | 2/2001 | Amano et al. |
| 6,197,018 B1 | 3/2001 | O'Donnell, Jr. |
| 6,197,056 B1 | 3/2001 | Schachar |
| 6,203,538 B1 | 3/2001 | Peyman |
| 6,210,401 B1 | 4/2001 | Lai |
| 6,258,082 B1 * | 7/2001 | Lin .............................. 606/5 |
| 6,263,879 B1 | 7/2001 | Lin |
| 6,280,435 B1 * | 8/2001 | Odrich et al. .................. 606/5 |
| 6,364,871 B1 | 4/2002 | Sotiropoulos et al. |
| 6,745,775 B2 * | 6/2004 | Lin ........................... 128/898 |
| 6,824,540 B1 | 11/2004 | Lin |
| 2001/0029363 A1 | 10/2001 | Lin |
| 2003/0220630 A1 | 11/2003 | Lin et al. |

* cited by examiner

METHODS AND APPARATUS FOR PRESBYOPIA CORRECTION USING ULTRAVIOLET AND INFRARED LASERS

This application is a continuation of application Ser. No. 09/820,832 (filed 30 Mar. 2001) now abandoned, which is a continuation-in-part of application Ser. No. 09/303,673 (filed 3 May 1999) now U.S. Pat. No. 6,258,082.

BACKGROUND OF THE INVENTION

1. Field of the Invention

The present invention relates to apparatus and methods for the treatment of presbyopia using ultraviolet and infrared lasers to ablate the sclera tissue of an eye.

2. Prior Art

Corneal reshaping, including a procedure called photorefractive keratectomy (PRK) and a new procedure called laser assisted in situ keratomileusis, or laser intrastroma keratomileusis (LASIK), has been performed by lasers in the ultraviolet (UV) wavelength of 193-213 nm. Commercial UV refractive lasers include ArF excimer lasers at 193 nm and other non-excimer, solid-state lasers, such as the one patented by the present inventor in 1992 (U.S. Pat. No. 5,144,630). Precise, stable corneal reshaping requires lasers with strong tissue absorption (or minimum penetration depth) such that the thermal damage zone is at a minimum (less than few microns). Furthermore, accuracy of the procedure of vision correction depends on the amount of tissue removed in each laser pulse, in the order of about 0.2 microns. Therefore, lasers at UV wavelengths between 193 and 213 nm and at the mid-infrared wavelengths between 2.8 and 3.2 microns are two attractive wavelength ranges which match the absorption peak of protein and water, respectively.

The above-described prior arts are however limited to the use of reshaping the corneal surface curvature for the correction of myopia, astigmatism and hyperopia. When a person reaches a certain age (around 45), the eyes start to lose their capability to focus for near vision and become presbyopic. Presbyopia is not due to the cornea curvature but comes about as the lens loses its ability to accommodate or focus for near vision as a result of loss of elasticity that is inevitable as people age. Therefore the existing lasers using corneal reshaping can not provide the solution for presbyopia patients. In addition, corneal reshaping is ablating the central portion of the cornea and changing its curvature.

To correct presbyopia, the present patent uses a "cold" laser to remove sclera tissue (outside the limbus area) versus a "thermal" lasers in Sand's patent (U.S. Pat. No. 5,484,432) to shrink the corneal shape (inside the limbus area). The cold laser of the present has a wavelength range of (0.15-0.36) microns and (2.6-3.2) microns which are also different from that of the "thermal" laser range of (1.80-2.55) microns proposed by Sand.

The prior arts of Ruitz (U.S. Pat. No. 5,533,997) and Lin (U.S. Pat. No. 5,520,679) are all limited to the corneal central portion and are designed to change the curvature of the cornea by ablation of the surface layer of the cornea. The present system, on the contrary, does not change the corneal central curvature and only ablates tissue outside the limbus.

The technique used in the prior art of Bille (U.S. Pat. No. 4,907,586) is specified to below conditions: (a) quasi-continuous laser having pulse duration less than 10 picoseconds and focused spot less than 10 micron diameter; (b) the laser is confined to the interior of a selected tissue to correct myopia, hyperopia or astigmatism, and (c) the laser is focused into the lens of an eye to prevent presbyopia. He also proposed to use laser to create a cavity within the corneal stroma to change its visco-elastic properties.

The "presbyopia" correction proposed by Ruitz using an excimer (ArF) laser also required the corneal surface to be reshaped to form a "multifocal" effect for a presbyopia patients to see near and far. However, Ruitz's "presbyopia" correction is fundamentally different from that of the present system which does not change the corneal curvature and only ablate the scleral tissue outside the limbus area. In the present system, we propose that the presbyopia patient is treated by increasing the patient's accommodation rather than reshaping the cornea into a "multifocal" configuration.

To treat presbyopic patients, or the reversal of presbyopia, using the concept of expanding the sclera by mechanical devices or implantation of a band has been proposed by Schachar in U.S. Pat. Nos. 5,489,299, 5,722,952, 5,465,737 and 5,354,331. These mechanical approaches have the drawbacks of complexity and are time consuming, costly and have potential side effects. To treat presbyopia, the Schachar U.S. Pat. Nos. 5,529,076 and 5,722,952 propose the use of heat or radiation on the corneal epithelium to arrest the growth of the crystalline lens and also propose the use of lasers to ablate portions of the thickness of the sclera. However, these prior arts do not present any details or practical methods or laser parameters for the presbyopic corrections. No clinical studies have been practiced to show the effectiveness of the proposed concepts. The concepts proposed in the Schachar patents regarding lasers suitable for ablating the sclera tissues were incorrect because many of his proposed lasers are thermal lasers which will cause thermal burning of the cornea, rather than tissue ablation. Furthermore, the clinical issues, such as locations, patterns and depth of the sclera tissue removal were not indicated in these prior patents. In addition, Schachar's methods also require the weakening of the sclera and increase the lens diameter by band expansion, which is different from the theory proposed in the present patent, where the sclera tissue becomes more flexible than weakening after laser ablation.

Another prior art proposed by Spencer Thornton, Chapter 4, "Survey for hyperopia and presbyopia", edited by Neal Sher (Williams & Wilkins, MD, 1997) is to use a diamond knife to incise radial cuts around the limbus areas. It requires a deep (90%-98%) cut of the sclera tissue in order to obtain accommodation of the lens. This method, however, involves a lot of bleeding and is difficult to control the depth of the cut which requires extensive surgeon's skill. Another major drawback for presbyopia correction provided by the above-described non-laser methods is the post-operative regression of about (30%-80%) caused by the healing of the "incision" gap. And this regression is minimum in the laser "excision" or "ablation" method proposed in the present invention.

The important concept proposed in the present invention is to support the present inventor's post-operative results which show minimum regression. We proposed a theory based upon the fact that the laser ablated sclera tissue "gap" will be filled in by the sub-conjunctiva tissue within few days after the surgery. This filled in sub-conjunctiva tissue is much more flexible than the original sclera tissue. Therefore the filled-in gap in the sclera area will cause the underlying ciliary body to have more space to move. This in turn, will allow the ciliary body to contract or expand the zonular fiber which is connected to the lens, when the presbyopic patient is adjusting his lens curvature to see near and far. The above described sub-conjunctiva tissue filling effects and the increase of "flexibility" of the sclera area are fundamentally different from the scleral "expansion" (or weakening) concept proposed by the prior arts of Schachar who proposed an implanted sclera band. In the present invention, the laser ablated sclera area is not weakening, it becomes more flexible instead.

Therefore one objective of the present invention is to provide an apparatus and method to obviate these drawbacks in the above described prior arts.

It is yet another objective of the present system to use a scanning device such that the degree of ciliary muscle accommodation can be controlled by the location, size and shape of the removed sclera tissue.

It is yet another objective of the present invention to define the non-thermal lasers for efficient tissue ablation.

It Is yet another objective of the present system to define the optimal laser parameters and the ablation patterns for the best clinical outcome for presbyopia patients, where scleral ablation will increase the accommodation of the ciliary muscle by the increase of the flexibility in the laser-ablated areas.

It is yet another objective of the present system to provide the appropriate scanning patterns which will cause effective ciliary body contraction and expansion of the zonules and the corneal lens based upon a theory different from the prior art. It is yet another objective of the present system to provide a new mechanism which supports the clinical results of laser presbyopia correction with minimum regression. One important concept proposed in the present system is to support the post-operative results which show minimum regression when presbyopia is corrected by a laser ablation of the sclera tissue. We proposed that the laser ablated sclera tissue "gap" is filled in by the sub-conjunctiva tissue within a few days after the surgery. This filled-in sub-conjunctiva tissue is much more flexible than the original sclera tissue. Therefore the flexible filled-in gap in the sclera area will allow the ciliary body to contract and cause the zonular fiber and the corneal lens to adjust its focusing power and increase the accommodation of presbyopic patient.

The concept presented in the present patent is to remove, by any methods including laser or non-laser methods, portion of the sclera tissue which is then filled in by sub-conjunctiva tissue to increase the flexibility of the scleral area and in turn causes the movement of the ciliary body and zonular fiber to increase the lens accommodation.

SUMMARY OF THE INVENTION

The preferred embodiments of the present surgical laser consists of a combination of an ablative-type laser and delivery unit. The ablative-type laser has a wavelength range of from 0.15 to 0.35 microns and from 2.6 to 3.2 microns and is operated in a pulsed mode such that the thermal damage of the corneal tissue is minimized.

It is yet another preferred embodiment of the present surgical laser to provide a scanning mechanism to effectively ablate the sclera tissue at a controlled depth by beam overlapping or by controlling the number of laser pulses acting on the sclera.

It is yet another embodiment of the present surgical laser to provide an integration system in which the ablative laser may be delivered by a scanner or by a fiber-coupled device which can be manually scanned over the cornea.

It is yet another embodiment of the present surgical laser to focus the laser beams to generate the sclera ablation patterns in radial lines, curved lines, dotted rings, or a slit pattern.

It is yet another embodiment of the present surgical laser to provide an integration system in which the sclera ablation leads to the increase of the accommodation of the ciliary muscle for the treatment of presbyopia.

Further preferred embodiments of the present surgical laser will become apparent from the description of the invention which follows.

DETAILED DESCRIPTION OF THE INVENTION AND THE PREFERRED EMBODIMENTS

Figure 1:
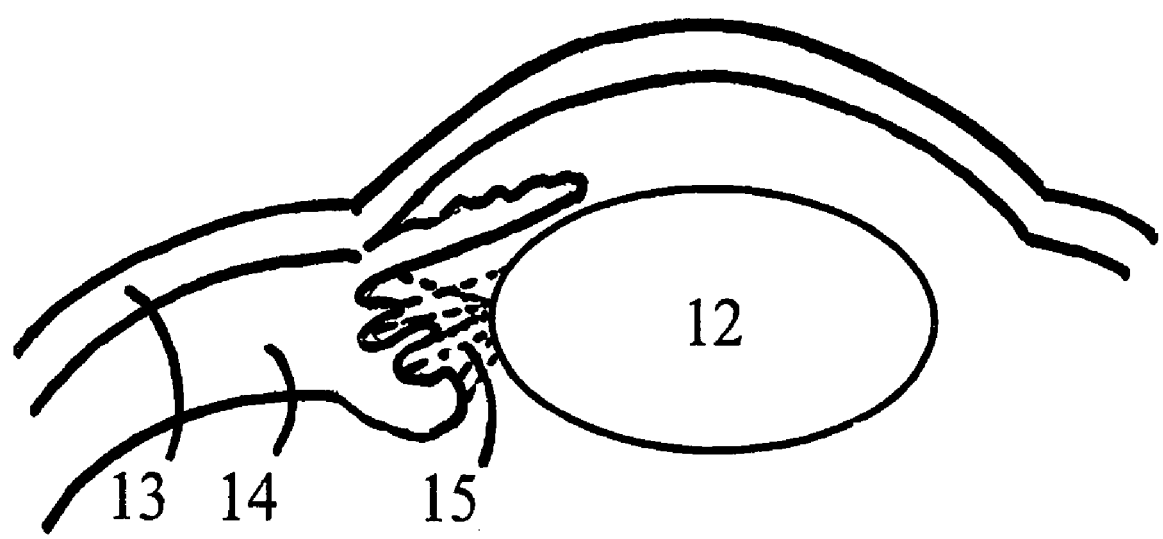
FIG. 1 is the schematic drawing of the anterposterior section through the anterior portion of a human eye showing the sclera, ciliary muscle, zonule and the lens.

FIG. 1 shows the lens of a human eye 12 connected to the scleral tissue 13 and the ciliary body 14 by zonule fibers 15. The lens power is adjusted by contraction and expansion of the ciliary muscle 14 and the movement of the zonular fiber 15 connected to the lens 12.

Figure 2:
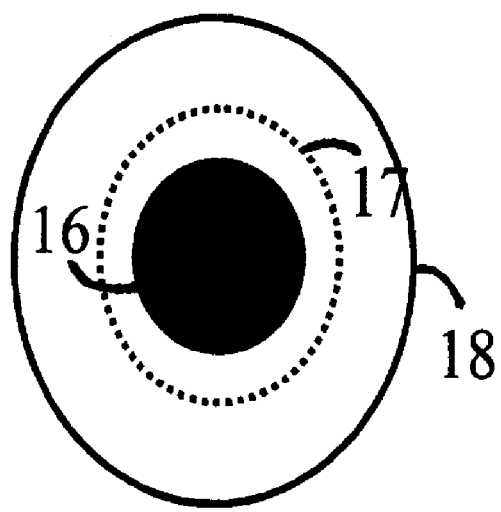
FIG. 2 is a schematic of a scleral ablation area outside the limbus.

FIG. 2 shows the laser ablated sclera area outside the limbus 16 defined by the area between two circles, 17 and 18, having diameter of about 10 mm and 18 mm. Various ablation patterns within these two circle area are proposed in the present invention.

Figure 3:
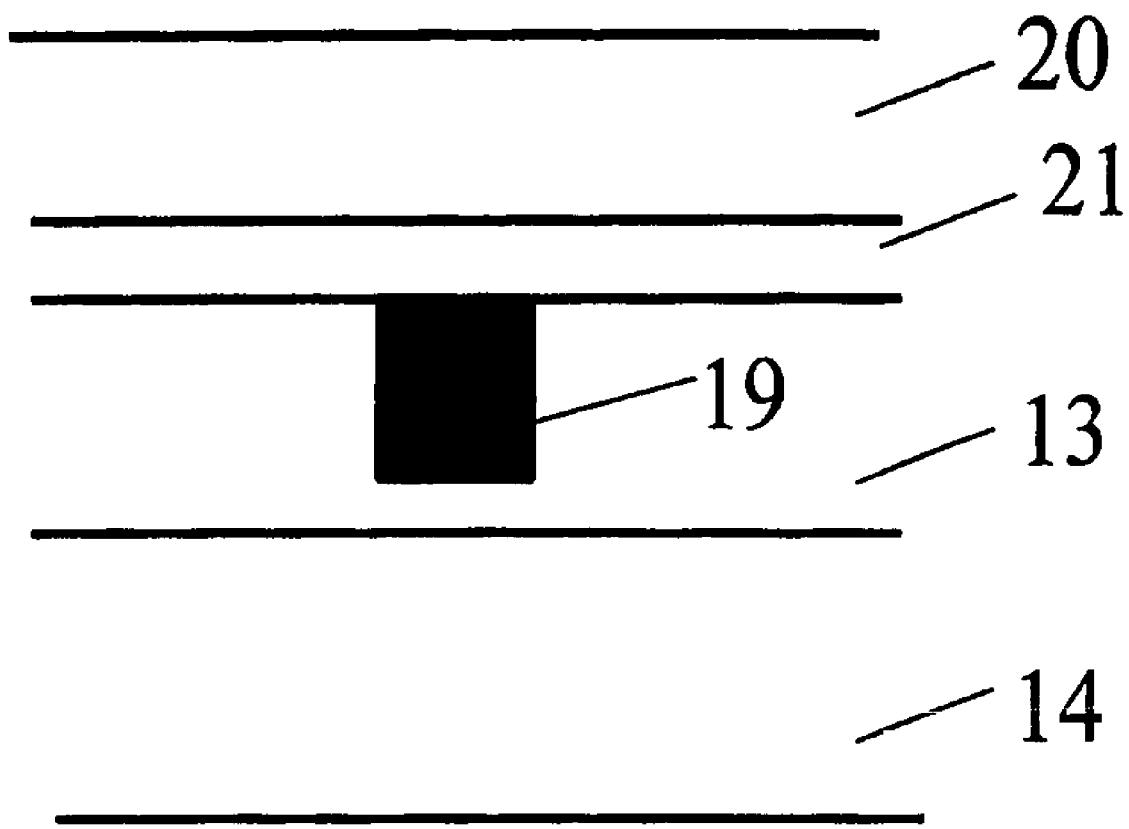
FIG. 3 is a schematic of the structure of an eye including the conjunctiva, sub-conjunctiva and scleral area ablated by laser.

Based on the proposed theory of the present invention and as shown in FIG. 3, when a portion of the sclera tissue 13 is removed by an ablative laser, this ablated "gap" 19 will be filled in by the sub-conjunctiva tissue 21 which is much more flexible than the original sclera tissue 13. This filled in sub-conjunctiva 21 will allow the ciliary body 14 to contract or relax the zonular fiber 15 which is connected to the lens, when the presbyopic patient is adjusting his lens curvature to see near and far. Ablation of the sclera 13 will cause the ciliary body 14 to contract and the lens 12 becomes more spherical in topography with a shorter radii of curvature for near objects. The reversed process of ciliary muscle relaxation will cause a longer radii of curvature for distant objects. Therefore, laser ablation of the sclera tissue will increase the accommodation of the ciliary body for the presbyopic patient to see both near and distance. Typically, we open the conjunctiva tissue 20 first and then ablate the sclera tissue 13. The conjunctiva 20 and sub-conjunctiva 21 layers may be remove mechanically by the same laser used for scleral ablation.

For efficient accommodation, the depth of the laser ablation needs to be approximately (60%-90%) of the sclera thickness which is about (500-700) microns. For safety reasons, the ablation depth should not cut through the choroid. It is therefore clinically important that the patient's sclera thickness be measured pre-operatively and the laser ablation depth controlled. A scanning laser is used to control this depth by the number of scanning lines or pulses over the selected area at a given set of laser parameters. Alternatively, the surgeon may observe the color change of the ablated sclera tissue to determine when the ablation depth reaches the interface of the sclera and the ciliary.

The ablation patterns can be any symmetric shapes around the limbus area, including radial lines, arc or curved line, dotted rings. These are examples only but it can be more or less without departing from the spirit and scope of the invention. Enhancement may be performed by adding more ablation lines. The preferred embodiment of the beam spot sizes are about (0.1-2.0) mm on the cornea surface for a round beam and about (0.1-2.0) mm in width and (2.0-5.0) mm in length for a line-spot These round and slit spots may be generated by a focusing spherical and a cylinder lens. These beam spots may also be generated by a "mask" which blocks the laser beam and produce the desired patterns on the cornea surface. The mask shall be made by non-transparent materials at the laser wavelength used for sclera ablation.

Ablation patterns described above may be generated by the preferred embodiment of the present system including a computer-controlled galvanometer, fiber-coupled hand piece (using a manual scan), motorized mirrors, refractive optics, reflecting mirror and any a translation device. A mask having various "holes" or "slits" may also be used to generate various patterns proposed in the present invention.

We are able to calibrate the ablation rate of various lasers on the sclera tissue by comparing the clinical data. To avoid the post-operative regression, the sclera tissue is permanently removed by the ablative lasers and filled in by the sub-conjunctiva tissues.

The preferred embodiment of the laser in the proposed system includes an ablative laser such as a Er:YAG laser; Er:YSGG laser; an optical parametric oscillation (OPO) laser at (2.6-3.2) microns; a gas laser with a wavelength of (2.6-3.2) microns; an excimer laser of ArF at 193 nm; a XeCl excimer laser at 308 nm; a frequency-shifted solid state laser at (0.15-3.2) microns; the harmonic generation of Nd:YAG or Nd:YLF or Ti:sapphire laser at wavelength of about (190-220) nm; a CO laser at about 6.0 microns and a carbon dioxide laser at 10.6 microns; a diode laser at (0.8-2.1) microns, or any other gas or solid state lasers including flash-lamp and diode-laser pumped, at (0.5-6.0) microns spectra range. To achieve the ablation of the sclera tissue at the preferred laser spot size of (0.1-2.0) mm requires an ablative laser energy per pulse of about (0.1-3.0) mJ depending on the pulse duration and the laser beam spot size.

For a typical pulse laser width of 100 nanoseconds to 500 microseconds, the preferred embodiments of FIG. 1 shall require the ablative laser to meet the peaks of tissue absorption spectra such as 0.98, 1.5, 2.1, 2.94 and 6.0 microns. However, for the case of lasers with a very short pulse of about from 1 femtosecond to 100 picoseconds, the laser wavelength becomes non-critical in the tissue interaction and the high peak laser intensity with small laser spot are more important. Therefore, The preferred embodiment of the laser should also include the short pulse lasers having wavelength of about (0.5-1.4) microns, such as Nd:YAG or Nd:YLF laser and their second harmonics operated in the range of picosecond or femtosecond pulse width. These short pulse lasers shall be able to remove sclera tissue and conjunctiva tissue easily by focusing the laser beam on the surface of the tissue to be removed. Another preferred embodiment of the present laser system is to tightly focused underneath the conjunctiva layer and selectively ablate the sclera tissue without damage or removing the conjunctiva tissue. Focused spot size of about (1-500) microns and accurate laser position of the depth will be needed for the procedure. We noted that the tissue reaction is not critical to the wavelength when the laser highly focused and achieve a high fluency level such that tissue can be removed by interruption process. Another preferred embodiment is to use an optical fiber or an articulate arm to deliver the ablative laser beams such that the presbyopia treatment may be conducted manually without the need of a scanner or reflecting mirrors. For the fiber delivered system, a fiber tip connected to the fiber hand piece is preferred such that sterilization may be done only on the fiber tip.

The concept presented in the present patent is to remove, by any methods laser or non-laser, portion of the sclera tissue which is filled in by sub-conjunctiva tissue to increase the flexibility of the scleral area and in turn causes the zonular fiber to increase the lens accommodation. Therefore the laser ablation effects on the scleral tissue may also be conducted by any non-laser methods such as using a diamond knife which removes the scleral tissue at a width about (0.5-2.0) mm and length of (2.0-4.0) mm, as far as this area can be filled in by the sub-conjunctiva tissue.

Another important concept proposed in the present invention is to support the post-operative results which show minimum regression. We proposed that the laser ablated sclera tissue "gap" will be filled in by the sub-conjunctiva tissue within few days after the surgery. This filled in sub-conjunctiva tissue is much more flexible than the original sclera tissue. Therefore the filled-in gap in the sclera area will cause the underlying ciliary body to contract or expand the zonular fiber and the lens when the presbyopic patient is adjusting the corneal lens power to see near and far.

To remove the sclera tissue, we typically open the conjunctiva first such that the underlying laser ablated area may be protected by the conjunctiva during the healing period. The preferred embodiment is to use mechanical method such as a knife or a scissors. Alternatively, the same ablative laser for sclera tissue ablation may be used to open (ablate) the conjunctiva. Another preferred embodiment is to couple the laser to a fiber which has a fiber tip having a size about (0.2-0.5) mm and can easily penetrate into the conjunctiva layer and ablate the sclera tissue underneath. Without opening the conjunctiva, the laser ablation procedure will be much less invasive to the cornea, because most of the bleeding during the procedure is caused by cutting the conjunctiva.

The invention having now been fully described, it should be understood that it may be embodied in other specific forms or variations without departing from the spirit or essential characteristics of the present invention. Accordingly, the embodiments described herein are to be considered to be illustrative and not restrictive.

I claim:

1. A laser beam ophthalmic surgery method for treating a presbyopic patient by measuring a thickness of a sclera tissue of an eye of a patient, opening a subconjunctiva tissue of the eye, forming a gap in the sclera tissue by removing between approximately 60% and approximately 90% of the sclera tissue thickness of the eye in a predetermined pattern and area, whereby the accommodation of the presbyopic eye increases via the movement of the ciliary body and zonular fiber connected to the lens of the eye, and allowing subconjunctiva tissue to fill the gap.

2. A laser beam ophthalmic surgery method for treating presbyopic patient by removing a portion of the sclera tissue of an eye in accordance with claim 1 in which said movement of the ciliary body is provided by the increase of the flexibility of said laser beam ablated sclera tissue which is filled in by sub-conjunctiva tissue.

3. A laser beam ophthalmic surgery method for treating presbyopic patient by removing portion of the sclera tissue of an eye in accordance with claim 1 in which said predetermined pattern includes at least 3 radial lines around the area of the cornea outside the limbus and each radial line has a dimension of about (0.1-1.0) mm in width and (2.0-5.0) mm in length.

4. A laser beam ophthalmic surgery method for treating presbyopic patient by removing portion of the sclera tissue of an eye in accordance with claim 1 in which said predetermined area is defined by the area outside the limbus and between two circles having diameter of about 10 mm and 18 mm.

5. A laser beam ophthalmic surgery method for treating presbyopic patient by removing portion of the sclera tissue of an eye in accordance with claim 1 in which said predetermined pattern includes at least 3 curved lines around the area of the cornea outside the limbus.

6. A laser beam ophthalmic surgery method for treating presbyopic patient by removing portion of the sclera tissue of an eye in accordance with claim 1 in which said predetermined pattern includes a dotted ring pattern around the area of the cornea outside the limbus and each dot has a size of about (0.1-2.0) mm in diameter.

7. A laser beam ophthalmic surgery method for treating presbyopic patient by removing portion of the sclera tissue of an eye in accordance with claims 1 in which said predetermined pattern is generated by a scanning mechanism.

8. A laser beam ophthalmic surgery method for treating presbyopic patient by removing portion of the sclera tissue of an eye in accordance with claim 1 in which said predetermined pattern is generated by a fiber-coupled device.

9. A laser beam ophthalmic surgery method for treating presbyopic patient by removing portion of the sclera tissue of an eye in accordance with claim 1 in which said predetermined pattern is generated by a translation device.

10. A laser beam ophthalmic surgery method for treating presbyopic patient by removing portion of the sclera tissue of an eye in accordance with claim 1 in which said predetermined pattern is generated by a mask which is non-transparent to the said laser beam.

11. A laser beam ophthalmic surgery method for treating presbyopic patient by removing portion of the sclera tissue of an eye in accordance with claim 1 in which said laser beam is a ultraviolet laser having a predetermined wavelength of about (0.15-0.36) microns.

12. A laser beam ophthalmic surgery method for treating presbyopic patient by removing portion of the sclera tissue of an eye in accordance with claim 1 in which said laser beam is an infrared laser having a predetermined wavelength of about (0.9-6.0) microns.

13. A laser beam ophthalmic surgery method for treating presbyopic patient by removing a portion of the scleral tissue of an eye in accordance with claim 12 in which said laser beam is tightly focused to a spot size of about (1-500) microns to selectively remove the sclera tissue underneath the conjunctiva layer.

14. A laser beam ophthalmic surgery method for treating presbyopic patient by removing portion of the sclera tissue of an eye in accordance with claim 1 in which said laser beam is a short pulse solid state laser having a predetermined wavelength of about (0.5-1.4) microns and a pulse width of about one femtosecond to one nanoseconds.

15. A laser beam ophthalmic surgery method for treating presbyopic patient by removing a portion of the sclera tissue of an eye in accordance with claim 1 in which said laser beam is delivered to said predetermined area of the cornea by an optical fiber.

16. A laser beam ophthalmic surgery method for treating presbyopic patient by removing a portion of the sclera tissue of an eye in accordance with claim 1 in which said sclera tissue is ablated by said laser beam after the conjunctiva is open.

17. A laser beam ophthalmic surgery method for treating presbyopic patient by removing a portion of the scleral tissue of an eye in accordance with claim 1, wherein the step of measuring comprises measuring the patient's scleral thickness preoperatively.

18. A laser beam ophthalmic surgery method for treating presbyopic patient by removing a portion of the scleral tissue of an eye in accordance with claim 1, wherein the step of measuring comprises observing a color change of the ablated sclera tissue.

19. A laser beam ophthalmic surgery method for treating a presbyopic patient by measuring a thickness of a sclera tissue of an eye of a patient, removing between approximately 60% and approximately 90% of the sclera tissue thickness of the eye in a predetermined pattern and area, whereby the accommodation of the presbyopic eye increases via the movement of the ciliary body and zonular fiber connected to the lens of the eye, in which said scleral tissue is ablated by said laser beam without opening the conjunctiva.

20. The method according to claim 19, wherein the step of measuring comprises measuring a thickness of the sclera preoperatively.

21. The method according to claim 19, wherein the step of measuring comprises observing the color change of the sclera tissue.

22. A method of treating a presbyopic eye using a laser beam, the method comprising removing scleral tissue from the presbyopic eye in a predetermined pattern and area, wherein the scleral tissue is removed to form a gap having a depth of between about 400 μm and 700 μm, allowing a conjunctiva tissue of the eye to fill the gap in the scleral tissue without implanting an implant into the gap, and whereby accommodation of the presbyopic eye increases via movement of the ciliary body and zonular fiber connected to the lens of the presbyopic eye.

23. The method of claim 22, wherein:
movement of the ciliary body is provided by sub-conjunctival tissue that is filled in where the scleral tissue is removed; and
the sub-conjunctival tissue has an increased flexibility compared to the scleral tissue.

24. The method of claim 22, wherein:
the predetermined pattern includes at least 3 radial lines around the area of the cornea outside the limbus; and
each radial line has a dimension between about 0.1 mm and about 1.0 mm in width and between about 2.0 mm and about 5.0 mm in length.

25. The method of claim 22, wherein the predetermined area is defined by the area outside the limbus and between two circles having diameter of between about 10 mm and about 18 mm.

26. The method of claim 22, wherein the predetermined pattern includes at least 3 curved lines around the area of the cornea outside the limbus.

27. The method of claim 22, wherein the predetermined pattern includes a dotted ring pattern around the area of the cornea outside the limbus and each dot has a size of between about 0.1 mm and about 2.0 mm in diameter.

28. The method of claim 22, wherein the predetermined pattern is generated by a scanning mechanism.

29. The method of claim 22, wherein the predetermined pattern is generated by a fiber-coupled device.

30. The method of claim 22, wherein the predetermined pattern is generated by a translation device.

31. The method of claim 22, wherein the predetermined pattern is generated by a mask which is non-transparent to the said laser beam.

32. The method of claim 22, wherein the laser beam has a wavelength between about 0.15 µm and about 0.36 µm.

33. The method of claim 22, wherein the laser beam has a wavelength between about 0.9 µm and about 6.0 µm.

34. The method of claim 22, wherein the laser beam is generated by a short pulse solid state laser having a wavelength between about 0.5 µm and about 1.4 µm, and a pulse width between about one femtosecond and one nanosecond.

35. The method of claim 22, wherein the laser beam is delivered to the predetermined area by an optical fiber.

36. The method of claim 22, wherein the scleral tissue is ablated by the laser beam after the conjunctiva is open.

37. The method of claim 22, wherein the scleral tissue is ablated by said laser beam without opening the conjunctiva.

38. The method of claim 22, wherein the laser beam is focused to a spot size between about 1 µm and about 500 µm to selectively remove the sclera tissue underneath the conjunctiva layer.

39. A laser beam ophthalmic surgery method for treating a presbyopic patient by opening a subconjunctiva tissue of an eye of the patient, forming a plurality of gaps in a scleral tissue of the eye by removing a portion of the scleral tissue of the eye, determining if the gaps have reached a depth between approximately 60% and approximately 90% of the sclera tissue thickness by observing a color change of the remaining scleral tissue, whereby the accommodation of the presbyopic eye increases via the movement of the ciliary body and zonular fiber connected to the lens of the eye, and allowing subconjunctiva tissue to fill a plurality of the gaps.

* * * * *